United States Patent [19]
Wright et al.

[11] Patent Number: 6,150,332
[45] Date of Patent: *Nov. 21, 2000

[54] METHOD AND COMPOSITION FOR LOWERING LOW DENSITY LIPOPROTEIN CHOLESTEROL

[75] Inventors: H. Tonie Wright, Richmond, Va.; S. Janciauskiene, Malmo, Sweden

[73] Assignee: Virginia Commonwealth University, Richmond, Va.

[ * ] Notice: This patent is subject to a terminal disclaimer.

[21] Appl. No.: 09/038,935

[22] Filed: Mar. 12, 1998

Related U.S. Application Data

[63] Continuation-in-part of application No. 08/781,020, Jan. 9, 1997, Pat. No. 5,792,749.
[51] Int. Cl.$^7$ .......................... A61K 38/08; A61K 38/04; C07K 7/06
[52] U.S. Cl. ........................... 514/16; 514/824; 530/328; 530/329
[58] Field of Search ........................ 514/12, 16; 530/328, 530/329, 324

[56] References Cited

U.S. PATENT DOCUMENTS 5,792,749  8/1998  Wright ...................................... 514/12

OTHER PUBLICATIONS

Ngo, J.T. et al. In: The Protein Folding Problem and tertiiary structure prediction. Eds. K. Merz, S. LeGrand. Birkhauser, Boston, p. 492–495, 1994.

Database CaPlus, DN 126:130776. Sugano,M. et al. Hissu Aminosan Kenkyu linkai, 144, 16–19, Jan. 1995.

Kroon et al. Netherlands J. of Medicine, 51, 16–27, Jan. 1997.

Grove et al. J.Lipid Res., 32, 1889–1897, 1991.

Liu et al. Cell Growth and Differentiation, 4, 611–616, 1994.

*Primary Examiner*—Michael Borin
*Attorney, Agent, or Firm*—Whitham, Curtis & Whitham

[57] ABSTRACT

$\alpha_1$-antitrypsin and peptide fragments and derivatives thereof are used to upregulate low density lipoprotein (LDL) cholesterol receptor levels in the liver, and this results in a decrease in circulating LDL cholesterol levels in the patient's circulatory system. In particular, the fragments are:

Leu-Phe-Met-Gly-Lys-Val-Val-Asn (SEQ ID NO:16)

Phe-Met-Gly-Lys-Val-Val-Asn (SEQ ID NO:17).

13 Claims, 6 Drawing Sheets

METHOD AND COMPOSITION FOR LOWERING LOW DENSITY LIPOPROTEIN CHOLESTEROL

CROSS-REFERENCE TO RELATED APPLICATIONS

This application is a continuation-in-part (CIP) application of U.S. patent application Ser. No. 08/781,020, filed Jan. 9, 1997, now U.S. Pat. No. 5,792,749, and the complete contents of that application are herein incorporated by reference.

DESCRIPTION

Background of the Invention

1. Field of the Invention

The invention relates generally to methods and compositions used for lowering low density lipoprotein (LDL) cholesterol levels in patients and, more particularly, to the new use of a naturally occurring protein and fragments and derivatives thereof for lowering LDL cholesterol in the treatment of a wide variety of disorders including atherosclerosis, hypercholesterolemia, gallstones, etc.

2. Description of the Prior Art

Coleseterol is a monohydric secondary alcohol of the cyclopenenophenanthrene (4-ring fused) system, and is the most abundant sterol in humans and higher animals. It is found in all body tissues, especially the brain, spinal cord, and in animal fats or oils, and is the main constituent of gallstones. The human body utilizes cholesterol as the precursor of bile acids, steroid hormones, and provitamin $D_3$. Cholesterol is present in the body in part as a free sterol and in part esterified with higher fatty acids as a lipid in human blood serum.

High levels of serum cholesterol bound to low density lipoprotein, commonly referred to as "LDL cholesterol", is known to correlate strongly with the occurrence of atherosclerosis in humans. Pharmacological methods for lowering serum cholesterol levels currently employ small molecule inhibitors of specific enzymes of the cholesterol biosynthetic pathway. Proprietary drugs for the treatment of hypercholesterolemia (e.g., Mevacor® and Gemfibrozil®) are generally effective, but do have some side effects. Since cholesterol homeostasis is critical, perturbations to cholesterol levels can have profound consequences in some patients, particularly those with liver pathologies. Other side effects disqualify existing medications for some patients with hypercholesterolemia.

SUMMARY OF THE INVENTION

It is an object of this invention to provide a method and composition for lowering serum LDL cholesterol in human and animal patients.

According to the invention, $\alpha_1$-antitrypsin and cleaved peptide fragments thereof have been found to upregulate the LDL receptor levels in the liver. By providing a patient with $\alpha_1$-antitrypsin or certain cleaved peptide fragments thereof, the patient's level of circulating LDL cholesterol will be reduced due to the increased level of LDL cholesterol receptors in the liver cells.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION $\alpha_1$-antitrypsin is a glycoprotein that is the major serine protease inhibitor (serpin) of human serum. $\alpha_1$-antitrypsin is synthesized in the liver and is genetically polymorphic due to the presence of over twenty alleles. The compound is comprised of 394 amino acid residues and 3 carbohydrate side chains linked to asparagine residues, and is primarily used by the body to inhibit serine proteases, including neutrophil and leukocyte elastase, which degrade connective tissue. $\alpha_1$-antitrypsin has also been used therapeutically in the treatment of emphysema (Merck Index, $11^{th}$ ed., entry 751 at pg 114).

It has been observed that upon interaction with leukocyte elastase and other proteases, a peptide bond is cleaved in the $\alpha_1$-antitrypsin, changing its tertiary structure and rendering it inactive as an inhibitor. The population of cleaved $\alpha_1$-antitrypsin molecules is cleared from the circulation through receptors in the liver. The uptake of cleaved $\alpha_1$-antitrypsin molecules and/or the carboxyl terminal peptide of cleaved $\alpha_1$-antitrypsin by liver cells is especially high during conditions of inflammation and in the acute phase. These conditions are accompanied by hypocholesterolemia. It has been found that exogenous $\alpha_1$-antitrypsin, and fragments and derivatives thereof, can be used to increase the uptake of LDL cholesterol by cultured liver cells. The cause of this depletion of extracellular cholesterol is due to an increase in the number of LDL receptors in liver cells which take up the LDL-cholesterol complex.

This invention takes advantage of the fact that there is an increase in LDL receptor levels induced by the cleaved $\alpha_1$-antitrypsin and fragments and derivatives thereof Specifically, extracellular levels of LDL cholesterol can be reduced by providing the patient with a sufficient quantity of additional $\alpha_1$-antitrypsin or fragments or derivatives thereof. The cleaved $\alpha_1$-antitrypsin or its substituent peptides resulting from interaction with leukocyte elastase or other proteinase cleaving of the reactive site residue 358 are taken up by receptors in the liver and result in increased clearance of LDL-bound cholesterol through these receptors, and thereby decreased circulating levels of LDL.

The chemical forms of $\alpha_1$-antitrypsin with hypocholesterolemic activity include $\alpha_1$-antitrypsin (in the presence of proteases which cleave it at residue 358), $\alpha_1$-antitrypsin proteolytically cleaved at amino acid residue 358, a carboxyl terminal peptide of $\alpha_1$-antitrypsin after cleaving at amino acid residue 358 identified as Sequence ID No. 1, as well as sub-peptides of the carboxyl terminal peptide Sequence ID No. 1, including the twenty amino acid sub-peptide having Sequence ID NO.2. Peptides which are related to SEQ ID No. 1 may also be active, and these peptides are defined by Sequence ID Nos. 3–15. Good results have been obtained with seven and eight amino acid peptide sub-fragments of the carboxyl terminal peptide of α₁-antitrypsin which are designated by Sequence ID Nos. 16–17.

```
SEQ 1:   Ser Ile Pro Pro Glu Val Lys Phe Asn Lys Pro Phe Val Phe Leu Met Ile
         Glu Gln Asn Thr Lys Ser Pro Leu Phe Met Gly Lys Val Val Asn Pro Thr
         Gln Lys

SEQ 2:   Ile Glu Gln Asn Thr Lys Ser Pro Leu Phe Met Gly Lys Val Val Asn Pro
         Thr Gln Lys

SEQ 3:   Ser Thr Gln Val Arg Phe Thr Val Asp Arg Pro Phe Leu Phe Leu Ile Tyr
         Glu His Arg Thr Ser Cys Leu Leu Phe Met Gly Arg Val Ala Asn Pro Ser
         Arg Ser

SEQ 4:   Ser Leu Asn Pro Asn Arg Val Thr Phe Lys Ala Asn Arg Pro Phe Leu Val
         Phe Ile Arg Glu Val Pro Leu Asn Thr Ile Ile Phe Met Gly Arg Val Ala
         Asn Pro Cys Val Lys

SEQ 5:   Thr Leu Leu Val Phe Glu Val Gln Gln Pro Phe Leu Phe Val Leu Trp Asp
         Gln Gln His Lys Phe Pro Val Phe Met Gly Arg Val Tyr Asp Pro Arg Ala

SEQ 6:   Met Ala Pro Glu Glu Ile Ile Met Asp Arg Pro Phe Leu Phe Val Val Arg
         His Asn Pro Thr Gly Thr Val Leu Phe Met Gly Gln Val Met Glu Pro

SEQ 7:   Pro Glu Asn Thr Phe Leu His Pro Ile Ile Gln Ile Asp Arg Ser Phe Met
         Leu Leu Ile Leu Glu Arg Ser Thr Arg Ser Ile Leu Phe Leu Gly Lys Val
         Val Asn Pro Thr Glu Ala

SEQ 8:   Ser Ala Leu Val Glu Thr Arg Thr Ile Val Arg Phe Asn Arg Pro Phe Leu
         Met Ile Ile Val Pro Thr Asp Thr Gln Asn Ile Phe Phe Met Ser Lys Val
         Thr Asn Pro Lys Gln Ala

SEQ 9:   Met Ser Leu Ser Ser Phe Ser Val Asn Arg Pro Phe Leu Phe Phe Ile Phe
         Glu Asp Thr Thr Gly Leu Pro Leu Phe Val Gly Ser Val Arg Asn Pro Asn
         Pro Ser Ala Pro Arg Glu Leu

SEQ 10:  Ser Val Ser Glu Glu Phe Arg Ala Asp His Pro Phe Leu Phe Cys Ile Lys
         His Ile Ala Thr Asn Ala Val Leu Phe Phe Gly Arg Cys Val Ser Pro

SEQ 11:  Thr Gly His Gly Gly Pro Gln Phe Val Ala Asp His Pro Phe Leu Phe Leu
         Ile Met His Lys Ile Thr Lys Cys Ile Leu Phe Phe Gly Arg Phe Cys Ser Pro

SEQ 12:  Glu Val Leu Glu Val Thr Leu Asn Arg Pro Phe Leu Phe Ala Val Tyr Asp
         Gln Ser Ala Thr Ala Leu His Phe Leu Gly Arg Val Ala Asn Pro Leu Ser
         Thr Ala

SEQ 13:  Ser Lys Pro Ile Ile Leu Arg Phe Asn Gln Pro Phe Ile Ile Met Ile Phe
         Asp His Phe Thr Trp Ser Ser Leu Phe Leu Ala Arg Val Met Asn Pro Val

SEQ 14:  Ser Ala Arg Leu Asn Ser Gln Arg Leu Val Phe Asn Arg Pro Phe Leu Met
         Phe Ile Val Asp Asn Asn Ile Leu Phe Leu Gly Lys Val Asn Arg Pro

SEQ 15:  Ser Ser Pro Pro Trp Phe Ile Val Asp Arg Pro Phe Leu Phe Phe Ile Arg
         His Asn Pro Thr Gly Ala Val Leu Phe Met Gln Gly Ile Asn Lys Pro

SEQ 16   Leu Phe Met Gly Lys Val Val Asn

SEQ 17   Phe Met Gly Lys Val Val Asn
```

The above-mentioned chemical forms of $\alpha_1$-antitrypsin and derived peptides are active in both soluble and polymerized or fibrillar forms of high molecular weight (e.g., 3–300 or more repeats of the sequence).

The peptide fragments of $\alpha_1$-antitrypsin can be referred to as hypocholesterolemic peptides because, like $\alpha_1$-antitrypsin, they increase LDL receptor levels in liver cells. Thus, a patient can be provided with either $\alpha_1$-antitrypsin, or its hypocholesterolemic peptides, in order to reduce circulating LDL cholesterol by increasing LDL cholesterol receptor sites.

The carboxyl terminal peptide (SEQ ID No. 1) or fragments thereof (e.g., SEQ ID No. 2), or related peptides (SEQ ID Nos. 3–15) or sub-fragments (e.g., SEQ ID Nos. 16–17) may be preferred for use in the practice of this invention since both in their soluble, monomeric state, and in their high molecular weigh polymeric form they can up-regulate LDL receptor levels, and should be more easily prepared and delivered to and used by the patient. However, if a hypocholesterolemic peptide is chosen, it will need to be stable and active in vivo.

$\alpha_1$-antitrypsin can be purified from human serum or in non-glycosylated form from recombinant plasmids in bacterial cells carrying the gene for the protein according to methods known to one of ordinary skill in the art. The hypocholesterolemic peptides can be obtained by proteinase treatment of uncleaved $\alpha_1$-antitrypsin. With particular respect to the sub-fragments designated by SEQ ID Nos. 16–17, it is noted that these peptides have the advantage that they can be synthesized inexpensively by conventional solid phase peptide synthetic methods. Because the octapeptide and heptapeptides of SEQ ID Nos. 16–17 are small fragments of a naturally occurring human serum protein, no immune side effects are likely for the circulatory system, and their small size may have benefits in terms of stability, production, and deliverability to a patient. The α₁-antitrypsin or hypocholesterolemic peptides would preferably be provided to a patient by infusion, implant or slow delivery vehicle to establish micromolar concentrations. However, other methods of delivery including intraperitoneal, intravenous, sub-lingual, oral, and the like may be useful with the practice of this invention, and the α₁-antitrypsin or hypocholesterolemic peptides may be combined with a wide variety of compounds depending on the mode of delivery including saline, water, oils, emulsions, propellants (e.g., CFCs and HFCs), preservatives (e.g., BAK, parabens), binders (e.g., lactose), elixirs, syrups, etc. To avoid degradation from exoproteases and enhance stability, it will be understood by those of skill in the art that the hypocholesterolemic peptides may be derivatized with various agents including acetyl, tosyl, and other groups (e.g., myristoyl, benzoyl, and carbobenzoxy). For example, in the experiments reported in Example 2 below, SEQ ID NO. 16 was derivatized with an acetyl group at the Leucine end. Thus, treatment of patients according to this invention contemplates the delivery of the hypocholesterolemic peptides alone or in derivatized form, either soluble or as a suspended polymer, in combination with delivery vehicles and adjuvants, for the purpose of lowering LDL cholesterol. The dose provided should be sufficient to decrease circulating levels of LDL, and to increase LDL receptor levels. The dose may vary widely depending on the mode of delivery, the age and gender of the patient, and the patient's previous medical history.

The treatment methodology of this invention should avoid immune side effects because a naturally occurring human serum protein is being used and because the invention involves amplifying a natural regulatory circuit. It is novel and distinct from pharmacological agents currently in use to lower serum cholesterol levels in that it does not act either directly as an inhibitor of, or indirectly, by decreasing cholesterol biosynthesis.

α₁-antitrypsin and its hypocholesterolemic peptides (SEQ ID No. 1 and SEQ ID No. 2) have been tested experimentally on several parameters of cholesterol status in human HepG2 cells (a transformed cell line) and in rat hepatocytes (a normal, but non-human line of liver cells). The results summarized below demonstrate a cross-species reactivity which points to the generality of the effect and is consistent with the high sequence similarity between the rat and human hypocholesterolemic peptides. In the results below, proteolytically cleaved α₁-antitrypsin is identified as "cleaved", the carboxyl terminal sequence SEQ 1 is identified as "C-36", the sub-peptide fragment SEQ 2 is identified as "C-20", and SEQ ID No. 16 as "C-8".

EXAMPLE 1

Figure 1A:
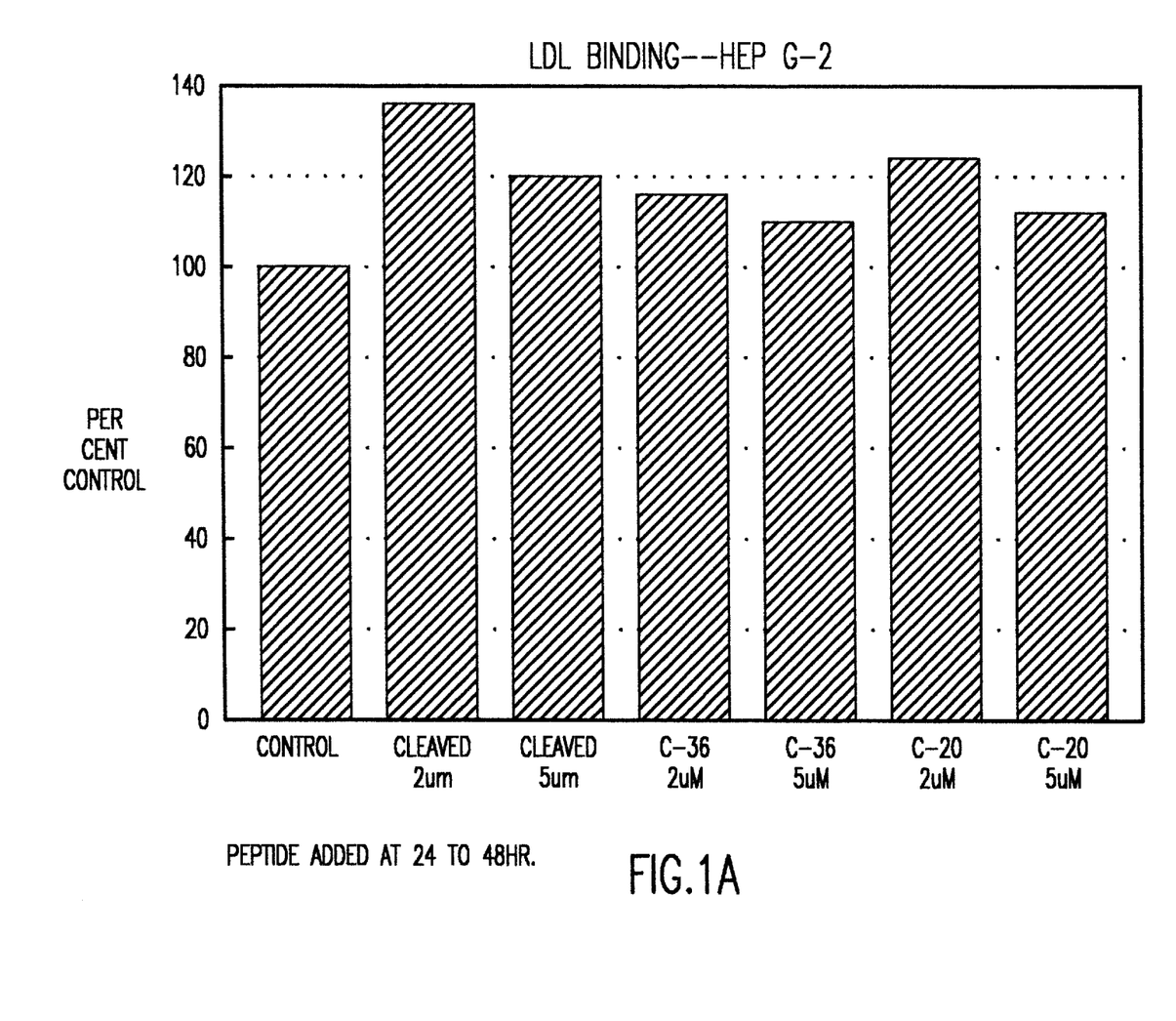
FIGS. 1a–b are bar graphs showing LDL binding in human HepG2 cells and rat hepatocytes, respectively.
Figure 1B:
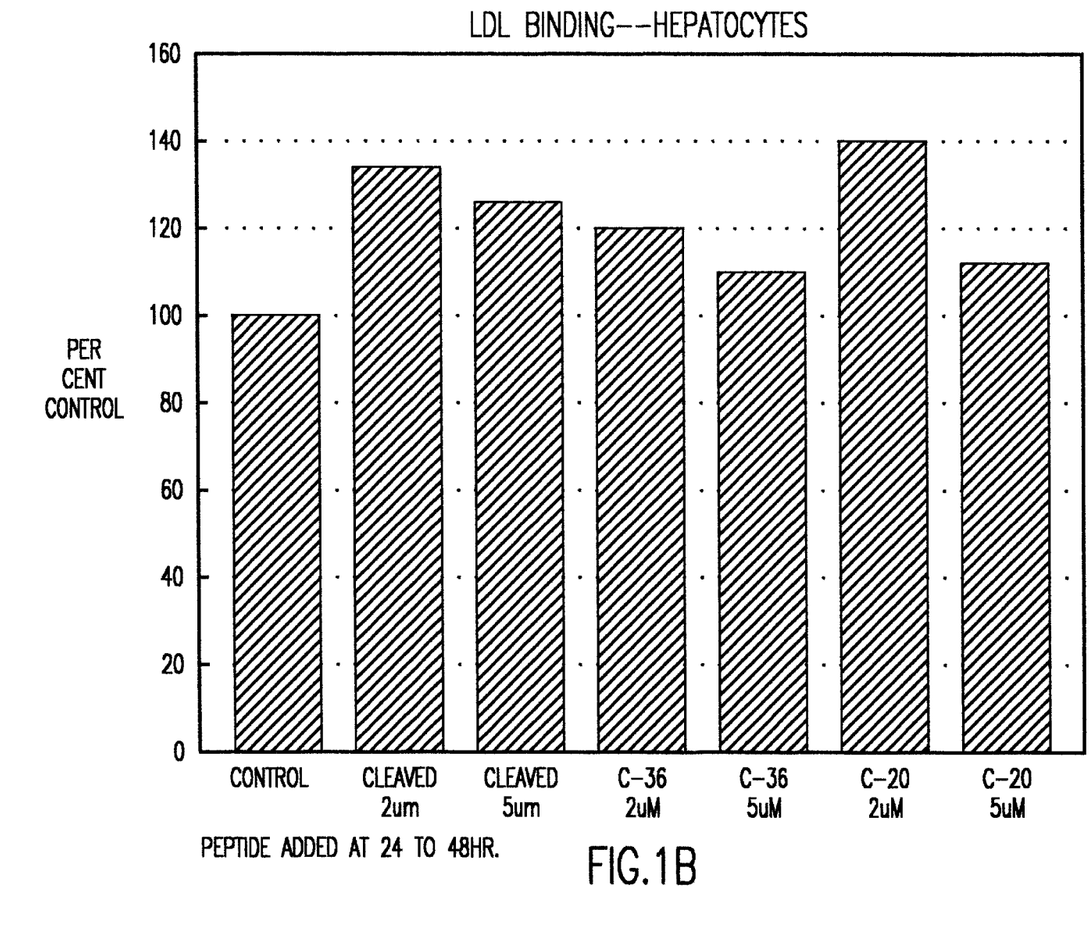

With reference to FIGS. 1a–b, an experiment was conducted wherein iodine labeled LDL was incubated with HepG2 or rat hepatocytes in culture with and without cleaved α₁-antitrypsin or hypocholesterolemic peptides. The cleaved α₁-antitrypsin and hypocholesterolemic peptides were added 24–48 hr after incubation began in 2 micromolar (μM) or 5 μM concentrations. The bound LDL was quantitated by counting. The control indicates the amount of bound LDL obtained when no cleaved α₁-antitrypsin or hypocholesterolemic peptides are present. FIGS. 1a–b show maximum LDL binding occurs when 2 μM α₁-antitrypsin or its peptide derivatives are added.

Figure 2:
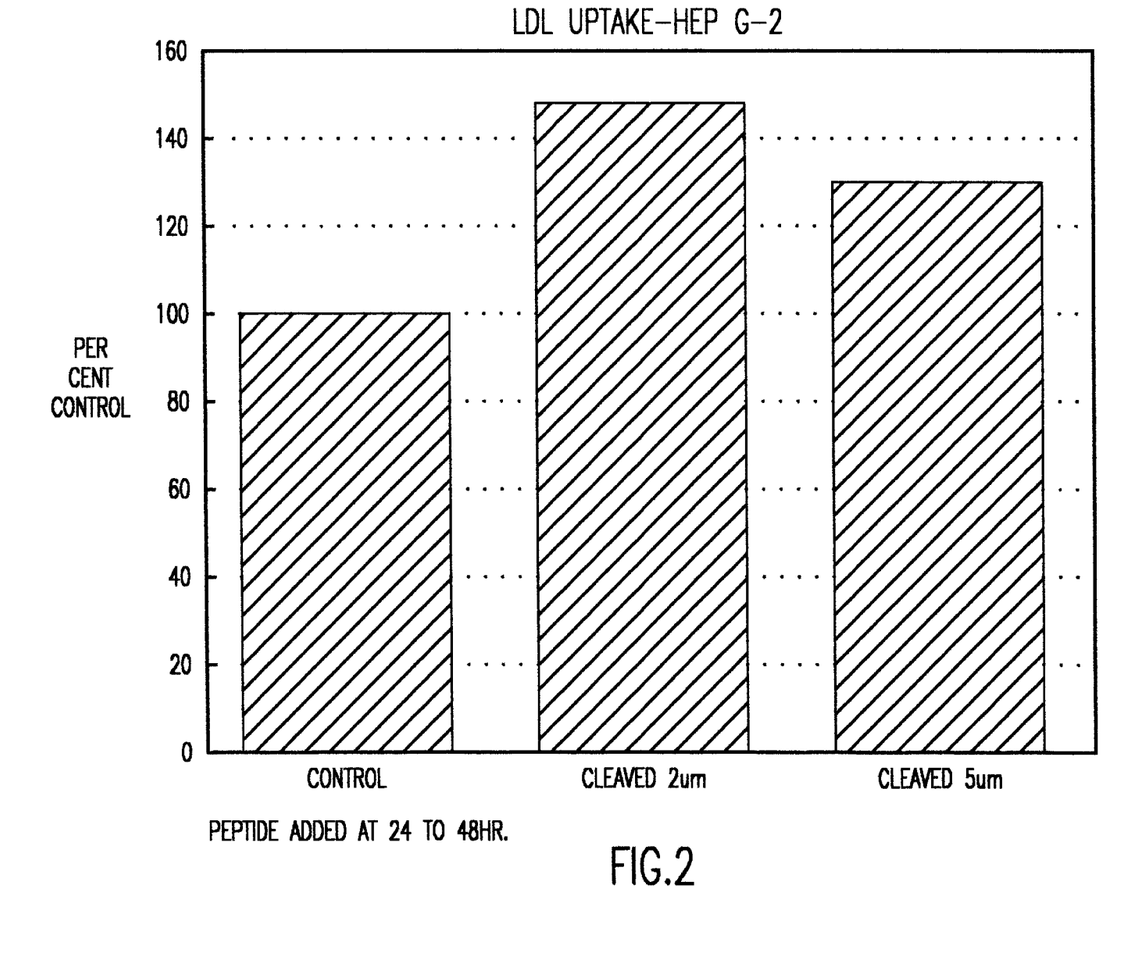
FIG. 2 is a bar graph showing LDL uptake in human HepG2 cells.

FIG. 2 shows internalized counts of LDL in HepG2 cells. FIG. 2 shows that LDL is taken up in response to the cleaved α₁-antitrypsin and hypocholesterolemic peptides. This demonstrates that the increased number of LDL receptors induced by α₁-antitrypsin and hypocholesterolemic peptides (FIGS. 1a–b) are competent to remove LDL from the external milieu (hepatic circulation, in vivo) to the cell cytosol, where further metabolic conversions occur.

Figure 3A:
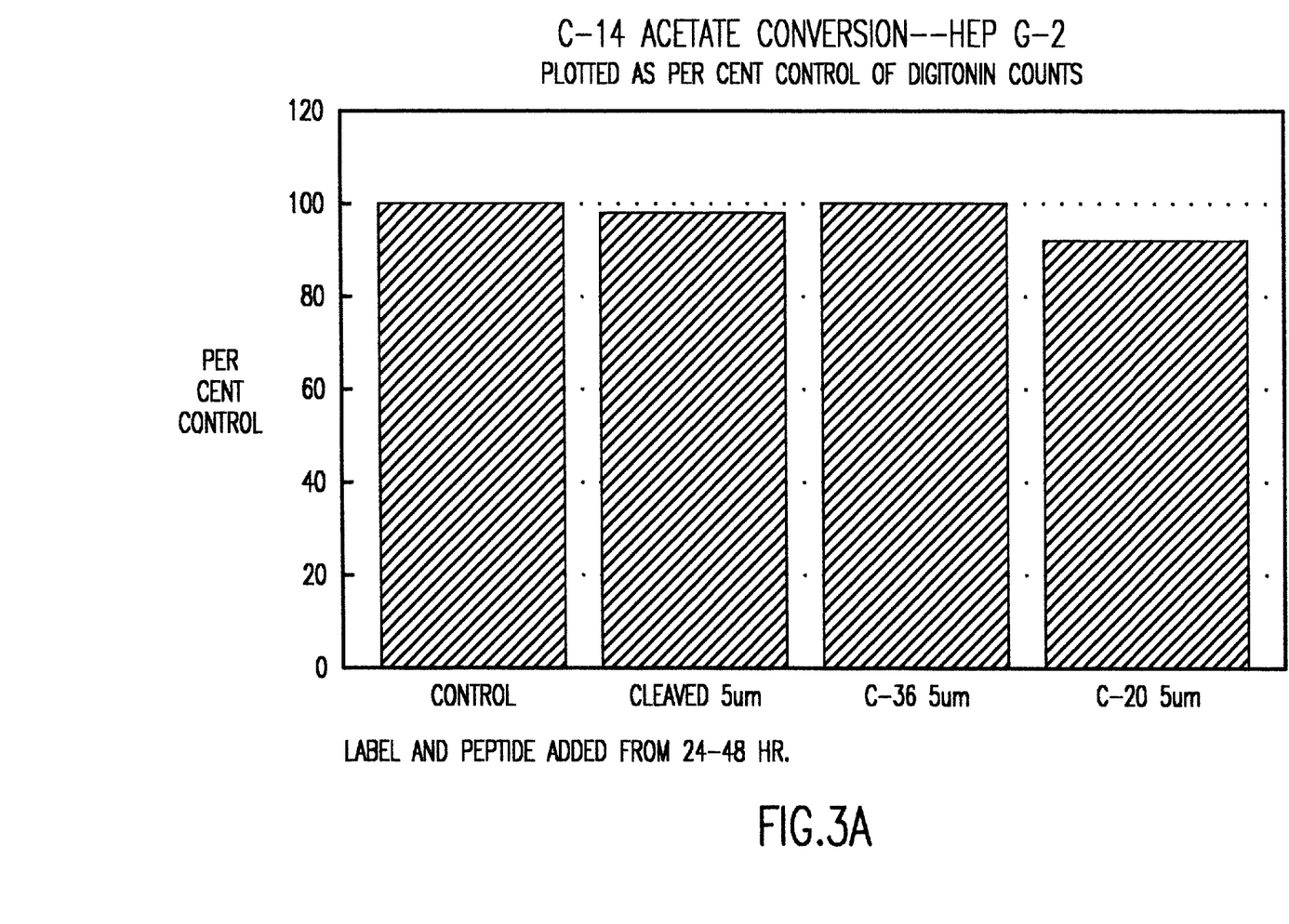
FIGS. 3a–b are bar graphs showing changes in acetate conversion in human HepG2 and rat hepatocytes, respectively, as a measure of cholesterol biosynthesis.
Figure 3B:
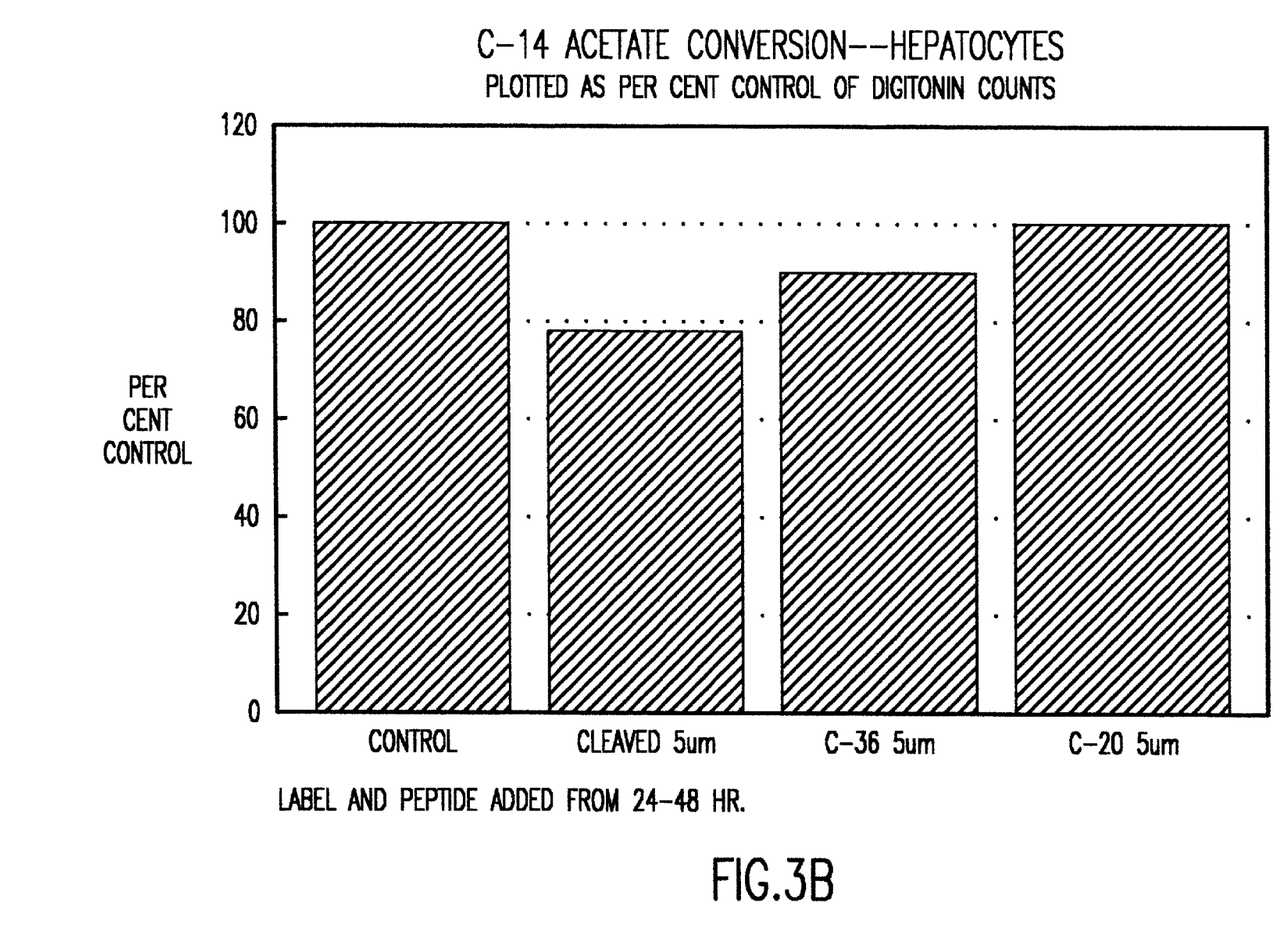

FIGS. 3a–b show the effects of α₁-antitrypsin and hypocholesterolemic peptides on de novo cholesterol biosynthesis being monitored by using $^{14}$C-labeled precursor acetate and extracting newly synthesized, labeled cholesterol with digitonin for counting. FIGS. 3a–b provide a measure of the changes in cholesterol biosynthesis, and demonstrate there is no up-regulation of cholesterol biosynthesis for the peptides studied.

The results in FIGS. 1–3 indicate that cleaved α₁-antitrypsin and hypocholesterolemic peptides can be used to decrease circulating LDL cholesterol by increasing LDL binding and uptake due to increased LDL binding sites, and that cholesterol homeostasis is broken in that there is no compensating up-regulation of de novo cholesterol synthesis.

EXAMPLE 2

Figure 4:
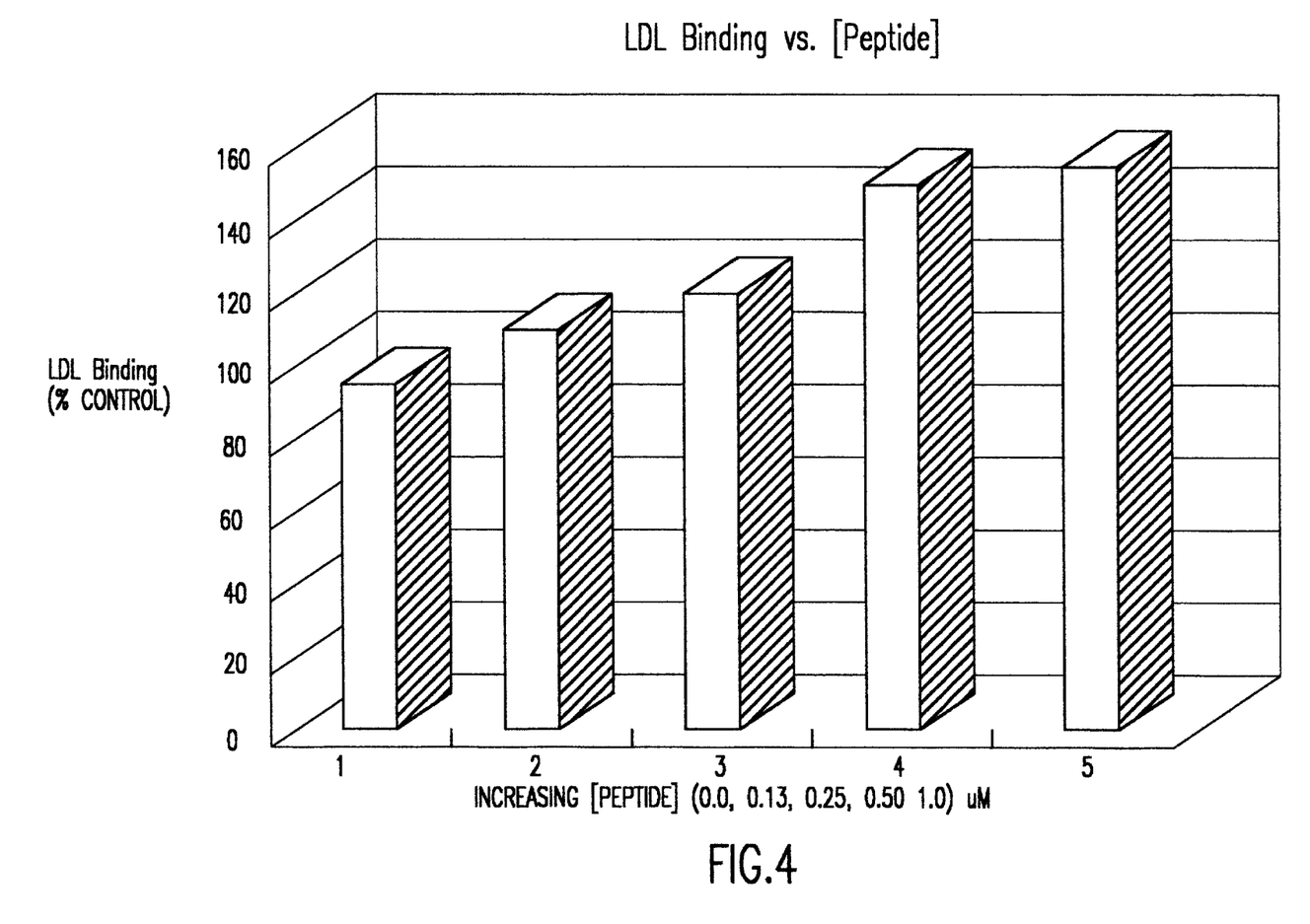
FIG. 4 is a bar graph similar to FIGS. 1a–b showing LDL binding in human HepG2 cells.

An acetyl derivative of SEQ ID No. 16 was tested experimentally in human Hep G2 cells for LDL binding in the same manner as described above in connection with FIGS. 1a–b. For example, FIG. 4 shows results where HepG2 cells were incubated with iodine labeled LDL in culture without α₁-antitrypsin or hypocholesterolemic peptides, and with varying amounts of the an acetyl derivative subfragment of α₁-antitrypsin identified as SEQ. ID No. 16. The sub-fragment was added 24–48 hours after incubation began in concentrations ranging from 0.13–1.4 μM. FIG. 4 shows that LDL binding increased with increasing concentrations of the sub-fragment.

While the invention has been described in terms of its preferred embodiments, those skilled in the art will recognize that the invention can be practiced with modification within the spirit and scope of the appended claims.

---

We claim:

1. A method for lowering low density lipoprotein cholesterol in a patient in need thereof, comprising the step of administering to said patient a sufficient quantity of a compound selected from the group consisting of SEQ ID NO. 16 and SEQ ID NO. 17, or derivative of said compound at amino terminus, to increase the level of low density lipoprotein cholesterol receptors.

2. The method of claim 1 wherein said compound is SEQ ID NO 16.

3. The method of claim 1 wherein said derivative at an amino terminus is selected from the group consisting of acetyl, tosyl, myristoyl, benzoyl, and carbobenzoxy.

4. The method of claim 1 wherein said derivative is an acetyl derivative of SEQ ID NO. 16.

5. The method of claim 1 wherein said compound is SEQ ID NO. 17.

6. The method of claim 1 wherein said compound in provided in soluble monomeric form.

7. The method of claim 1 wherein said compound is provided in polymeric fibrillar form.

8. A method for lowering low density lipoprotein cholesterol in a patient in need thereof, comprising the step of administering to said patient a sufficient quantity of a compound selected from the group consisting of SEQ ID NO. 16 and SEQ ID NO. 17 , or derivative of said compound at amino terminus to lower low density lipoprotein cholesterol in said patient.

9. The method of claim 8 wherein said compound is SEQ ID NO. 16.

10. The method of claim 8 wherein said compound is SEQ ID NO. 17.

11. The method of claim 8 wherein said compound is provided in soluble monomeric form.

12. The method of claim 8 wherein said compound is provided in polymeric fibrillar form.

13. The method of claim 8 wherein said derivative at an amino terminus is selected from the group consisting of acetyl, tosyl, myristoyl, benzoyl, and carbobenzoxy.

* * * * *

SEQUENCE LISTING

<160> NUMBER OF SEQ ID NOS: 17

<210> SEQ ID NO 1
<211> LENGTH: 36
<212> TYPE: PRT
<213> ORGANISM: Homo sapiens

<400> SEQUENCE: 1

-continued

Ser Ile Pro Pro Glu Val Lys Phe Asn Lys Pro Phe Val Phe Leu Met
 1               5                  10                  15

Ile Glu Gln Asn Thr Lys Ser Pro Leu Phe Met Gly Lys Val Val Asn
            20                  25                  30

Pro Thr Gln Lys
        35

<210> SEQ ID NO 2
<211> LENGTH: 20
<212> TYPE: PRT
<213> ORGANISM: Homo sapiens

<400> SEQUENCE: 2

Ile Glu Gln Asn Thr Lys Ser Pro Leu Phe Met Gly Lys Val Val Asn
 1               5                  10                  15

Pro Thr Gln Lys
            20

<210> SEQ ID NO 3
<211> LENGTH: 36
<212> TYPE: PRT
<213> ORGANISM: Homo sapiens

<400> SEQUENCE: 3

Ser Thr Gln Val Arg Phe Thr Val Asp Arg Pro Phe Leu Phe Leu Ile
 1               5                  10                  15

Tyr Glu His Arg Thr Ser Cys Leu Leu Phe Met Gly Arg Val Ala Asn
            20                  25                  30

Pro Ser Arg Ser
        35

<210> SEQ ID NO 4
<211> LENGTH: 39
<212> TYPE: PRT
<213> ORGANISM: Homo sapiens

<400> SEQUENCE: 4

Ser Leu Asn Pro Asn Arg Val Thr Phe Lys Ala Asn Arg Pro Phe Leu
 1               5                  10                  15

Val Phe Ile Arg Glu Val Pro Leu Asn Thr Ile Ile Phe Met Gly Arg
            20                  25                  30

Val Ala Asn Pro Cys Val Lys
            35

<210> SEQ ID NO 5
<211> LENGTH: 34
<212> TYPE: PRT
<213> ORGANISM: Homo sapiens

<400> SEQUENCE: 5

Thr Leu Leu Val Phe Glu Val Gln Gln Pro Phe Leu Phe Val Leu Trp
 1               5                  10                  15

Asp Gln Gln His Lys Phe Pro Val Phe Met Gly Arg Val Tyr Asp Pro
            20                  25                  30

Arg Ala

<210> SEQ ID NO 6
<211> LENGTH: 33
<212> TYPE: PRT
<213> ORGANISM: Homo sapiens

```
<400> SEQUENCE: 6

Met Ala Pro Glu Glu Ile Ile Met Asp Arg Pro Phe Leu Phe Val Val
 1               5                  10                  15

Arg His Asn Pro Thr Gly Thr Val Leu Phe Met Gly Gln Val Met Glu
                20                  25                  30

Pro

<210> SEQ ID NO 7
<211> LENGTH: 40
<212> TYPE: PRT
<213> ORGANISM: Homo sapiens

<400> SEQUENCE: 7

Pro Glu Asn Thr Phe Leu His Pro Ile Ile Gln Ile Asp Arg Ser Phe
 1               5                  10                  15

Met Leu Leu Ile Leu Glu Arg Ser Thr Arg Ser Ile Leu Phe Leu Gly
                20                  25                  30

Lys Val Val Asn Pro Thr Glu Ala
            35                  40

<210> SEQ ID NO 8
<211> LENGTH: 40
<212> TYPE: PRT
<213> ORGANISM: Homo sapiens

<400> SEQUENCE: 8

Ser Ala Leu Val Glu Thr Arg Thr Ile Val Arg Phe Asn Arg Pro Phe
 1               5                  10                  15

Leu Met Ile Ile Val Pro Thr Asp Thr Gln Asn Ile Phe Phe Met Ser
                20                  25                  30

Lys Val Thr Asn Pro Lys Gln Ala
            35                  40

<210> SEQ ID NO 9
<211> LENGTH: 41
<212> TYPE: PRT
<213> ORGANISM: Homo sapiens

<400> SEQUENCE: 9

Met Ser Leu Ser Ser Phe Ser Val Asn Arg Pro Phe Leu Phe Phe Ile
 1               5                  10                  15

Phe Glu Asp Thr Thr Gly Leu Pro Leu Phe Val Gly Ser Val Arg Asn
                20                  25                  30

Pro Asn Pro Ser Ala Pro Arg Glu Leu
            35                  40

<210> SEQ ID NO 10
<211> LENGTH: 33
<212> TYPE: PRT
<213> ORGANISM: Homo sapiens

<400> SEQUENCE: 10

Ser Val Ser Glu Glu Phe Arg Ala Asp His Pro Phe Leu Phe Cys Ile
 1               5                  10                  15

Lys His Ile Ala Thr Asn Ala Val Leu Phe Phe Gly Arg Cys Val Ser
                20                  25                  30

Pro
```

```
<210> SEQ ID NO 11
<211> LENGTH: 35
<212> TYPE: PRT
<213> ORGANISM: Homo sapiens

<400> SEQUENCE: 11

Thr Gly His Gly Gly Pro Gln Phe Val Ala Asp His Pro Phe Leu Phe
 1               5                  10                  15

Leu Ile Met His Lys Ile Thr Lys Cys Ile Leu Phe Phe Gly Arg Phe
                20                  25                  30

Cys Ser Pro
         35

<210> SEQ ID NO 12
<211> LENGTH: 36
<212> TYPE: PRT
<213> ORGANISM: Homo sapiens

<400> SEQUENCE: 12

Glu Val Leu Glu Val Thr Leu Asn Arg Pro Phe Leu Phe Ala Val Tyr
 1               5                  10                  15

Asp Gln Ser Ala Thr Ala Leu His Phe Leu Gly Arg Val Ala Asn Pro
                20                  25                  30

Leu Ser Thr Ala
         35

<210> SEQ ID NO 13
<211> LENGTH: 34
<212> TYPE: PRT
<213> ORGANISM: Homo sapiens

<400> SEQUENCE: 13

Ser Lys Pro Ile Ile Leu Arg Phe Asn Gln Pro Phe Ile Ile Met Ile
 1               5                  10                  15

Phe Asp His Phe Thr Trp Ser Ser Leu Phe Leu Ala Arg Val Met Asn
                20                  25                  30

Pro Val

<210> SEQ ID NO 14
<211> LENGTH: 33
<212> TYPE: PRT
<213> ORGANISM: Homo sapiens

<400> SEQUENCE: 14

Ser Ala Arg Leu Asn Ser Gln Arg Leu Val Phe Asn Arg Pro Phe Leu
 1               5                  10                  15

Met Phe Ile Val Asp Asn Asn Ile Leu Phe Leu Gly Lys Val Asn Arg
                20                  25                  30

Pro

<210> SEQ ID NO 15
<211> LENGTH: 33
<212> TYPE: PRT
<213> ORGANISM: Homo sapiens

<400> SEQUENCE: 15

Ser Ser Pro Pro Trp Phe Ile Val Asp Arg Pro Phe Leu Phe Phe Ile
 1               5                  10                  15

Arg His Asn Pro Thr Gly Ala Val Leu Phe Met Gly Gln Ile Asn Lys
                20                  25                  30
```

-continued

```
Pro

<210> SEQ ID NO 16
<211> LENGTH: 8
<212> TYPE: PRT
<213> ORGANISM: Homo sapiens

<400> SEQUENCE: 16

Leu Phe Met Gly Lys Val Val Asn
  1               5

<210> SEQ ID NO 17
<211> LENGTH: 7
<212> TYPE: PRT
<213> ORGANISM: Homo sapiens

<400> SEQUENCE: 17

Phe Met Gly Lys Val Val Asn
  1               5
```